US010594258B1

(12) United States Patent
Alkandary et al.

(10) Patent No.: US 10,594,258 B1
(45) Date of Patent: *Mar. 17, 2020

(54) DEVICE AND METHOD FOR MEASURING EFFECT OF SOILING ON PHOTOVOLTAIC DEVICE

(71) Applicant: KUWAIT INSTITUTE FOR SCIENTIFIC RESEARCH, Safat (KW)

(72) Inventors: Abdullah Ramadhan Alkandary, Qortuba (KW); Abdulwahab Tareq Alasfour, Abdulla Al-Mubarak (KW); Feras Ghazi Alzubi, Safat (KW)

(73) Assignee: Kuwait Institute for Scientific Research, Safat (KW)

( * ) Notice: Subject to any disclaimer, the term of this patent is extended or adjusted under 35 U.S.C. 154(b) by 0 days.

This patent is subject to a terminal disclaimer.

(21) Appl. No.: 16/528,587

(22) Filed: Jul. 31, 2019

Related U.S. Application Data

(63) Continuation-in-part of application No. 16/244,041, filed on Jan. 9, 2019, now Pat. No. 10,447,201.

(51) Int. Cl.
*G01R 31/00* (2006.01)
*H02S 50/10* (2014.01)
(Continued)

(52) U.S. Cl.
CPC .............. *H02S 50/10* (2014.12); *G01N 21/94* (2013.01); *G01R 29/24* (2013.01); *H01L 31/02021* (2013.01); *H02S 40/10* (2014.12)

(58) Field of Classification Search
CPC .... G01N 21/94; G01R 29/24; G01R 31/2605; G01R 31/40; G01R 31/405; G01R 31/025;
(Continued)

(56) References Cited

U.S. PATENT DOCUMENTS 4,712,063 A 12/1987 Osterwald et al.
8,951,356 B2 * 2/2015 Fisher .................... G06Q 50/06
134/18
(Continued)

FOREIGN PATENT DOCUMENTS

CN 108745998 A 11/2018

OTHER PUBLICATIONS

Micheli et al., "An Investigation of the Key Parameters for Predicting PV Soiling Losses," Progress in Photovoltaics, vol. 25, Issue 4, Jan. 25, 2017, pp. 269-337.

*Primary Examiner* — Thang X Le
(74) *Attorney, Agent, or Firm* — Richard C. Litman; Nath Goldberg & Meyer

(57) ABSTRACT

The device and method for measuring the effect of soiling on a photovoltaic device includes a device in which a photovoltaic device (reference solar cell, solar cells, PV module, etc.) may be shifted between partially and fully enclosed compartments in quick succession for measurements of the same device (1) when directly exposed to illumination or solar radiation; (2) when placed under a glass or transparent cover maintained cleared or cleaned of soil; and (3) when placed under glass or transparent cover left exposed to natural outdoor soiling, or attenuated using simulated soil that is not periodically cleaned. The measurements may be of short circuit current (Isc), maximum power (Pmax), or other electrical parameter conventionally used to evaluate performance of the photovoltaic device. A soiling ratio calculated as:

$$SR_{Pmax} = 1 - \frac{P_{max2} - P_{max3}}{P_{max1}}$$

(Continued)

or calculated as:

$$SR_{Isc} = 1 - \frac{I_{sc2} - I_{sc3}}{I_{sc1}}$$

may be used to compare or monitor performance of the photovoltaic device between measurement cycles.

19 Claims, 11 Drawing Sheets

(51) Int. Cl.
  *G01N 21/94* (2006.01)
  *H02S 40/10* (2014.01)
  *H01L 31/02* (2006.01)
  *G01R 29/24* (2006.01)

(58) Field of Classification Search
  CPC . G01R 31/024; G01R 31/42; H01L 31/02021; H02S 40/10
  See application file for complete search history.

(56) References Cited

U.S. PATENT DOCUMENTS

| | | | |
|---|---|---|---|
| 9,564,853 B2* | 2/2017 | Gostein | G01N 21/94 |
| 10,171,029 B2 | 1/2019 | Gostein et al. | |
| 2012/0053867 A1* | 3/2012 | Dunn | H02S 50/10 |
| | | | 702/58 |
| 2013/0159064 A1 | 6/2013 | Fisher et al. | |
| 2015/0090311 A1* | 4/2015 | Mau | H02S 50/10 |
| | | | 136/244 |
| 2015/0280644 A1 | 10/2015 | Gostein et al. | |
| 2016/0190984 A1* | 6/2016 | Caine | H02S 50/00 |
| | | | 702/60 |
| 2016/0359453 A1* | 12/2016 | Jones | H02S 50/00 |
| 2017/0104451 A1* | 4/2017 | Gostein | H02S 40/10 |
| 2017/0230001 A1 | 8/2017 | Gostein et al. | |
| 2017/0338771 A1 | 11/2017 | Gostein et al. | |
| 2018/0159469 A1 | 6/2018 | Trupke et al. | |
| 2018/0278202 A1 | 9/2018 | Gostein et al. | |
| 2018/0337633 A1 | 11/2018 | Tamizhmani et al. | |

* cited by examiner

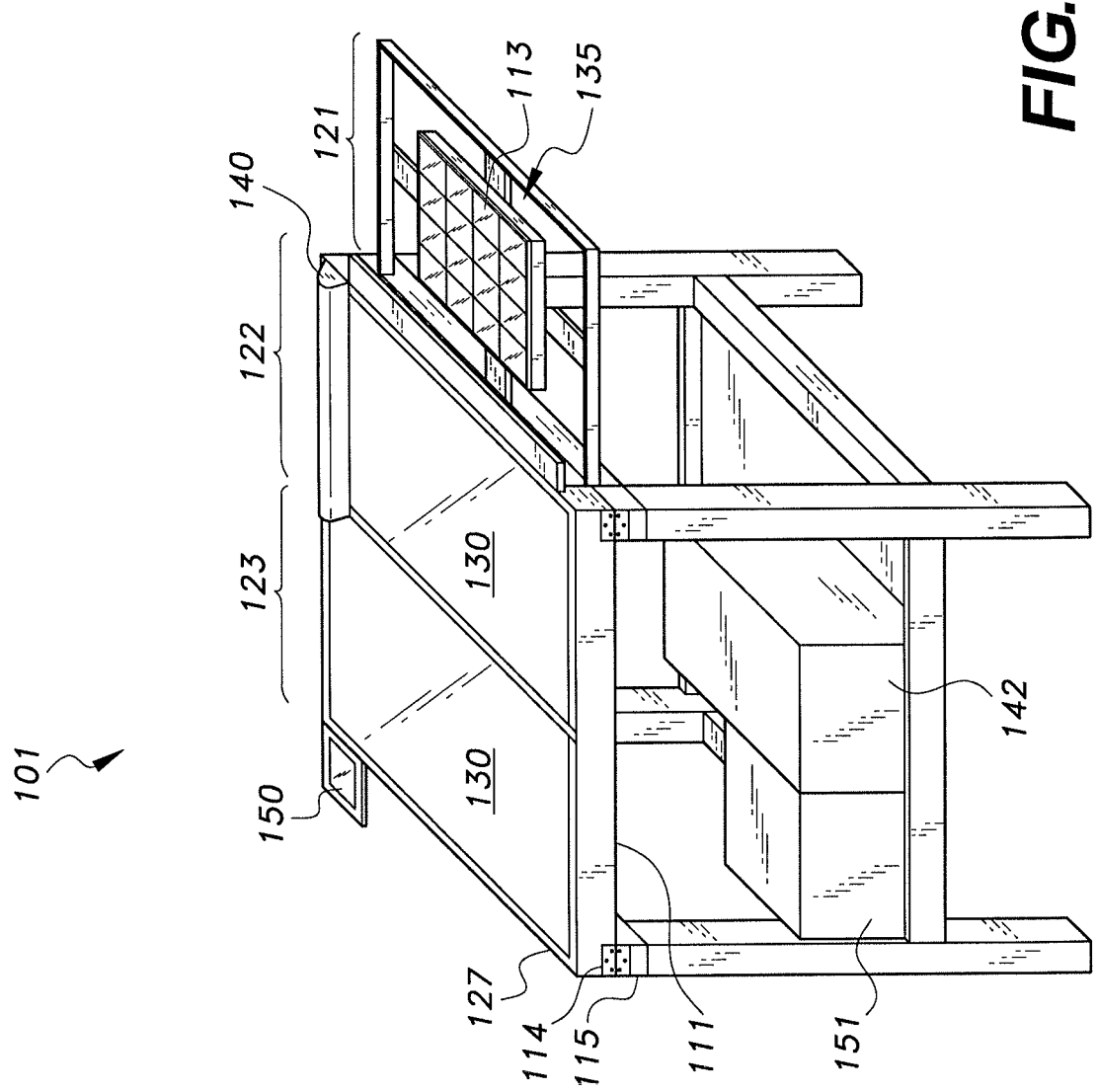

DEVICE AND METHOD FOR MEASURING EFFECT OF SOILING ON PHOTOVOLTAIC DEVICE

CROSS-REFERENCE TO RELATED APPLICATION

This application is a continuation-in-part of U.S. patent application Ser. No. 16/244,041, filed on Jan. 9, 2019.

BACKGROUND

1. Field

The present disclosure relates to measuring and testing of photovoltaic devices, and particularly to a device and method for measuring the effect of soiling on a photovoltaic device, such as a reference cell, a solar cell, or a photovoltaic module, to determine the change in electrical characteristics resulting from accumulated dust and other environmental contamination.

2. Description of the Related Art

One form of energy generation is the conversion of sunlight to electricity using a photovoltaic (PV) module that consists of electrically connected solar cells. When a group of modules are further connected, a PV system is formed, which typically ranges in size from residential to utility.

When PV systems are installed in outdoor locations, one of the most detrimental environmental factors that affects their performance is the accumulation of soil, which is the settlement of dust particles, debris, and/or other contaminants on the surface of PV modules, otherwise known as soiling. Performance degradation occurs because when particles settle on the surface of PV modules, they interfere with incoming light by blocking, attenuating, and/or scattering it. The power output that is lost as a result is known as the Soiling Loss (SL). Many research groups in dust-intensive regions have reported SL values well above 20%. For example, a PV system that was installed in a desert region tilted at 20°, lost up to 60% of its power after six months of no cleaning.

Such high soiling loss values result in significant revenue deficiencies and excessive operation and maintenance costs. Consequently, there has been a growing interest in quantifying and monitoring such an environmental factor, as the deployment of PV systems in dust-intensive climates is rapidly increasing. This is especially true for utility scale PV systems, as it improves energy prediction models, optimizes PV Plant cleaning strategies, and creates a new performance assessment tool.

Fundamentally, existing soiling detectors are implemented by measuring one of three primary parameters, viz., soil mass; light transmission; or PV performance. The latter parameter has been widely adopted by PV practitioners and researchers for directly measuring the power loss due to soiling. This method of soiling detection measurement involves comparing the power output of an installed reference PV device (i.e., cleaned daily) to a test PV device (i.e., left to naturally soil).

Although performance-based measurements using two PV devices offer a direct way to measure SL, the method involves high uncertainty, since it assumes that the two devices are identical. However, it is well established that PV devices fabricated using the same materials and processes have intrinsic differences. Such differences include (a) Quantum efficiency (QE); (b) Angular response (Ar); (c) Thermal response (Tr); (d) Parasitic resistances (Pr); and how these four parameters change over time.

Therefore, simply comparing two PV devices to measure soiling while neglecting the aforementioned differences will introduce high measurement uncertainty. Using this method, errors as high as 4.5% have been reported. Although a few researchers have considered accommodating such factors, their approaches require intensive periodic in-lab PV assessment, which renders them impractical for long-term monitoring. Furthermore, such an assessment is less than optimum for accommodating the particular environment of a given installation site.

Additionally, for the same amount of soiling particles on a PV module, non-uniform soiling distribution can cause more power output reduction than if the distribution is uniform, since current or power output for PV cells (or an array of PV modules) connected in series would be limited to the maximum output of the worst performing cell (or module). This is due to variant partial shading intensities on the PV surface, which results in electrical mismatch between interconnected solar cells of a single module, and may consequently introduce more PV array mismatch. While conventional technologies use image processing in conjunction with optical and thermal sensors, the resemblance of PV electrical performance in visual, optical, or thermal terms tends to develop uncertainties in determining soiling uniformity effects on PV devices. In addition, the comparison of two (or more) non-identical PV devices in some approaches would also increase uncertainties stemming from intrinsic differences between the PV devices.

Even with existing techniques for studying non-uniformity in soiling, there is still a need for an effective tool to better understand electrical performance variance across a PV module due to partial shading caused by non-uniform soiling distribution. Such a tool would aid in the detection of potential PV module defects due to current mismatch (i.e., hotspot formation). Further, there are presently difficulties in effectively simulating the electrical output losses of PV cells across a single module, which would be desirable to allow practitioners to further assess the occurrences of hot spots. On a larger scale, it would be desirable to allow PV plant designers and operators to study how soiling non-uniformity may affect a large array of PV modules connected in series and, hence, enhancing PV plant decisions with regard to preconstruction design layouts, maintenance urgency of highly non-uniform soiling locations, and better predictions of plant performance variance due to seasonal soiling distribution. Thus, a device and method for spatially resolving the effect of soiling non-uniformity on photovoltaics solving the aforementioned problems are desired.

SUMMARY

The device and method for measuring the effect of soiling on a photovoltaic (PV) device are used to provide data representative of deterioration in performance from soiling of PV devices. A test jig with a test enclosure having first, second and third measurement stations can be used. In this embodiment, the first station is substantially external to the test enclosure and is used to obtain reference values for a PV device as a device under test (DUT); this station will be interchangeably referred to as the initial state hereinafter. The second and third stations are within a test enclosure. A support for the DUT has the capability of transporting the PV device between the first, second and third stations for sequential testing on the same device under different conditions. At the first station, the DUT has substantially full, direct, unobstructed exposure to a light source, defining a first state. At the second station, the DUT has exposure through a transparent cover of the enclosure that is maintained in clean condition, defining a second state. In this regard, the transparent cover of the second compartment is adapted for a wide range of cleaning frequency (minutely, hourly, daily, etc.) At the third station, the DUT has exposure through a transparent cover of the enclosure that has been exposed to natural outdoor soiling, or attenuated using simulated soil, defining a third state. In the first state, the exposure comprises light passed directly to the PV device, substantially without passing through the enclosure. In the second state, the exposure comprises light passed to the PV device through the transparent cover in a clean state. In the third state, the exposure comprises light passed to the photovoltaic device through a transparent cover in a soiled state. A measuring and test unit is configured to measure short circuit current (Isc), maximum power (Pmax), and/or other criteria in the three states in quick succession and report the result in a novel ratio to show the loss in current or power resulting from soiling conditions. The device may be computerized to monitor changes in the ratio and/or store and manipulate data relating to the efficiency of the PV device under test. The disclosed technology serves as a platform for PV device testing under soiling conditions. It can accommodate any mono-facial PV technology, thus allowing for a wide range of potential applications.

In addition to the above, a soiling uniformity index associated with the third station may be calculated. An m×n Cartesian coordinate grid is associated with the transparent cover of the third station, on which natural or simulated soil is permitted to accumulate without cleaning. The grid values m and n are each integers greater than or equal to one. Measurements of the at least one electrical parameter of the single photovoltaic device at the third station are made at each Cartesian location (i,j), where i and j are each integers such that $1 \leq i \leq m$ and $1 \leq j \leq n$.

A soiling ratio is calculated at each Cartesian location (i,j) from the measurements taken at each Cartesian location (i,j) to define a two-dimensional matrix of soiling ratios. A soiling uniformity index associated with the DUT and the transparent cover on which natural or simulated soil is permitted to accumulate without cleaning can then be calculated based on the set of soiling ratios.

These and other features of the present disclosure will become readily apparent upon further review of the following specification and drawings.

BRIEF DESCRIPTION OF THE DRAWINGS

FIG. 1A is a perspective view of a device for measuring the effect of soiling on a photovoltaic device, shown in its east-west (E-W) lateral orientation and largely schematic.

Similar reference characters denote corresponding features consistently throughout the attached drawings.

DETAILED DESCRIPTION OF THE PREFERRED EMBODIMENTS

Figure 1B:
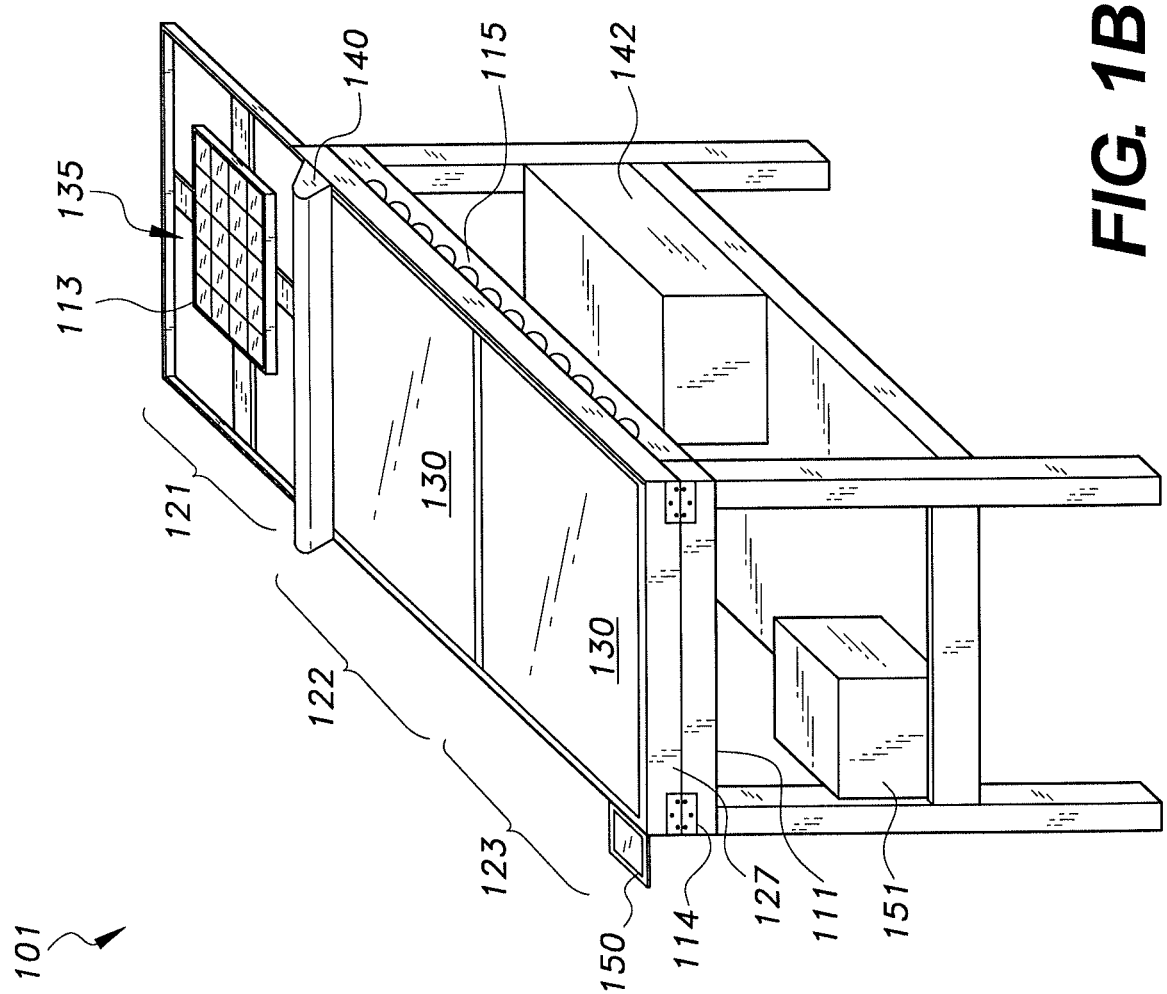
FIG. 1B is a perspective view of a device for measuring the effect of soiling on a photovoltaic device, shown in its north-south (N-S) axial orientation and largely schematic.

The device and method for measuring the effect of soiling on a photovoltaic (PV) device includes a device in which a PV device (solar cell, PV module, etc.) may be shifted between partially and fully enclosed compartments in quick succession for measurements of the same device (1) when directly exposed to illumination or solar radiation; (2) when placed under a transparent cover that is maintained to be cleared or cleaned of soil; and (3) when placed under a transparent cover left exposed to soiling that is not periodically cleaned. The measurements may be of short circuit current ($I_{sc}$), maximum power ($P_{max}$), and/or other parameters conventionally used to evaluate performance of the PV device. Each measurement may be an instantaneous value or a measurement of changing values over a predetermined time interval; e.g., an I-V curve. A soiling ratio calculated as:

$$SR_{Pmax} = 1 - \frac{P_{max2} - P_{max3}}{P_{max1}}$$

or calculated as:

$$SR_{Isc} = 1 - \frac{I_{sc2} - I_{sc3}}{I_{sc1}}$$

may be used to compare or monitor effectiveness of the PV device between measurement cycles.

To capture the soiling effect using a single device, the PV device is required to be measured under three different states. State 1 will be the initial state where the $I_{sc}$, $P_{max}$, and/or other parameters of the PV device are measured. The device will then move to State 2, and a similar measurement to the initial state, State 1, will be taken under a clean transparent cover. For the final state, State 3, the same measurement will be repeated under a soiled (i.e., never cleaned) transparent cover. Because the extra layer of transparent cover in States 2 and 3 will introduce an additional power loss, measurements in all three states need to be mathematically compensated for this extra layer. To further ensure accuracy, all three states will be measured in a sufficiently short period of time. Any deviations in PV temperature and/or amount of sunlight received from the states will be normalized. This process allows for the computation of the Soiling Ratio (SR) as an indicator of PV performance loss resulting from soiling. Since the new disclosed technology utilizes a single PV device, the SR will be expressed as:

$$SR_{Pmax} = \frac{P_{max\,dirty}}{P_{max\,clean}} = \frac{P_{max3} + (P_{max1} - P_{max2})}{P_{max1}} = 1 - \frac{P_{max2} - P_{max3}}{P_{max1}}$$

and/or as:

$$SR_{sc} = \frac{I_{sc3}(I_{sc1} - I_{sc2})}{I_{sc1}} = 1 - \frac{I_{sc2} - I_{sc3}}{I_{sc1}},$$

where SR is the Soiling Ratio, $P_{max}$ is the power at maximum power point, $I_{SC}$ is the short circuit current, and the subscripts 1, 2 and 3 refer to the State in which the measurement was made.

The use of a single PV device minimizes uncertainties stemming from complex differences that inherently exist between two similar, but nonidentical, devices. This provides a low-cost technique offering practical in-field use because it does not require cumbersome periodic operation and maintenance cycles. Furthermore, for an accurate soiling representation of a PV system, the user is not confined to a limited set of PV technologies (i.e., some products supply only one type), but broadens the scope of work to accommodate any desired mono-facial technology. Ultimately, the technique is intended to provide a reliable, practical and affordable soiling monitoring system for widespread applications that extend from research to industry. In particular, this technique advances the optimization of PV cleaning cycles and cost, optimization of PV plant site layout design, monitoring energy production losses due to soiling, studying the effectiveness of new anti-soiling surface coatings, assessing possible hotspot occurrences, and the collection of site-specific data.

According to the method, three consecutive $I_{SC}$, $P_{max}$, and/or other parameter measurements of the PV device are taken, first, under no transparent cover (State 1), then under a clean transparent cover (State 2), and finally under a soiled transparent cover (State 3). These measurements can be achieved in a sufficiently short period of time. Measuring one PV device can effectively eliminate the uncertainties stemming from two non-identical devices. The disclosed technology can be a standalone system where no external power supply is needed to allow installation in remote areas.

Software may be provided to enable the user to monitor and control the sensor system. Features such as data analysis, data presentation, and data extraction can be included because of the direct calculation of soiling loss. As part of the data acquisition system, software may be provided in any convenient form, such as a desktop, as web-based software, or using a handheld device. The software can also be integrated with the data acquisition system. The system may execute functions including, but not limited to, the following: receive data of physical variables; process data; provide a graphical user interface; offer analytic tools for researchers and industry; forecast and compute optimal cleaning time; export records and reports in text or other portable data formats; detect system faults; configure features of system hardware, such as motor and fan speeds; and integrate with standard SCADA systems for PV power plants. In addition to the above-mentioned features, the software may have built-in features that would allow a user, such as an administrator, to change the way data is organized, computed and filtered, which allows for device optimization.

FIGS. 1A and 1B are schematic diagrams of a device 101 configured for measuring the effect of soiling on a photovoltaic device, shown in a lateral configuration and in an axial configuration, respectively. In the latter configuration, the PV device is measured along the north-south direction rather than the east-west direction between states, which yields higher measurement accuracy and allows for new parameters to be evaluated. Depicted is a frame housing 111 for testing a PV device, such as a PV module component 113, as a device under test (DUT). The device 101 has three test stations, 121, 122, 123, corresponding to the three measurement states, State 1—initial, State 2—clean and State 3—soiled. Test station 121 is only partially enclosed, being exposed directly to the outside environment for receiving illumination or solar radiation, whereas test stations 122 and 123 are provided as an enclosed compartment portion 127 of the device 101. A transparent cover 130, such as a tempered PV glass, forms a top of enclosed portion 127. It is noted, however, that, at test station 123, the transparent cover 130 is soiled without any cleaning throughout the soiling monitoring cycle. The DUT 113 can be removed from its housing so that it can be characterized either by its original equipment manufacturer (OEM) or by an independent laboratory, when needed.

Nevertheless, the device 101 can be used to compare operational parameters in the three states, provided care is taken not to damage the DUT 113 during routine testing. In the device 101, the DUT is transported through stations 121, 122, and 123 to measure the electrical output at each station in a sufficiently short period of time such that environmental variations between the three measurements are kept to a minimum.

As can be seen in FIG. 1A, the DUT component 113 is shown outside of an enclosed portion of the device 101, but still supported by the device 101 at test station 121, corresponding to "State 1—initial". Both the DUT component 113 and the tray 135 holding it are coplanar with the other testing stations 122 and 123.

The DUT component 113 is then moved inside the device 101 to test station 122. Test station 122 is within the enclosed portion of the device 101, under a portion of the device 101 (a transparent cover 130) maintained in a clean state. Testing at test station 122 corresponds to "State 2—clean". In the enclosed portion of the device 101, light passes through a transparent cover 130, which, at test station 122, is maintained in a substantially clean condition.

The DUT component 113 is then moved inside the device 101 to test station 123. Test station 123 is within the enclosed portion 127 of the device 101, under a portion of the device 101 left in a soiled state. Testing at test station 123 corresponds to "State 3—soiled".

While a single enclosure is shown for test stations 122 and 123, it is understood that test stations 122 and 123 may be provided with separate enclosures, each with a separate transparent cover 130, but with station 123 in a soiled state. Likewise, a single test station can be used to provide the test operations of test stations 121, 122 and 123 with a single PV device, with the test station being changed by uncovering the DUT for State 1, covering the DUT with the clean transparent cover for State 2, and covering the DUT with the same or a different cover, but in a soiled state, for State 3.

The "State 3—soiled" condition can be adapted to outdoor local conditions. Examples of environmental debris or contamination can be dust from wind, vegetation debris, and soiling from birds or animal waste, all of which can vary according to the location of the test site.

The device 101 may have a support tray 135, which can be used to transport the DUT between the test stations, 121, 122, 123, either manually or automatically.

The device 101 is used to determine a performance difference between a clean state, described as "State 2—clean", and a soiled state, described as "State 3—soiled". The device 101 can then be used to determine the difference in electrical output when a PV device's surface becomes soiled.

Ventilation fans (not separately shown) may be used to reduce heat buildup until internal temperature and humidity sensor readings substantially agree with the ambient. When the DUT is at rest, and no measurements are being taken, the ventilation fans may operate to protect the internal components of the device 101 inside the enclosed compartment portion 127. Further, the enclosed compartment portion 127 can be opened for scheduled and unscheduled maintenance. The cleaning of the transparent cover 130 may be done either manually or automatically using a built-in washer 140.

The device 101 may have a tilting mechanism component 114, which can adjust the tilt angle of test stations 121, 122, 123, the tray component 135, and the DUT component 113 concurrently between 0° (i.e., parallel to the ground) and 90° (i.e., perpendicular to the ground), either manually or automatically. The device 101 may also have a water tank 142 connected to the washer 140, an irradiance sensor 150, and a monitoring and control unit 151.

Figure 2:
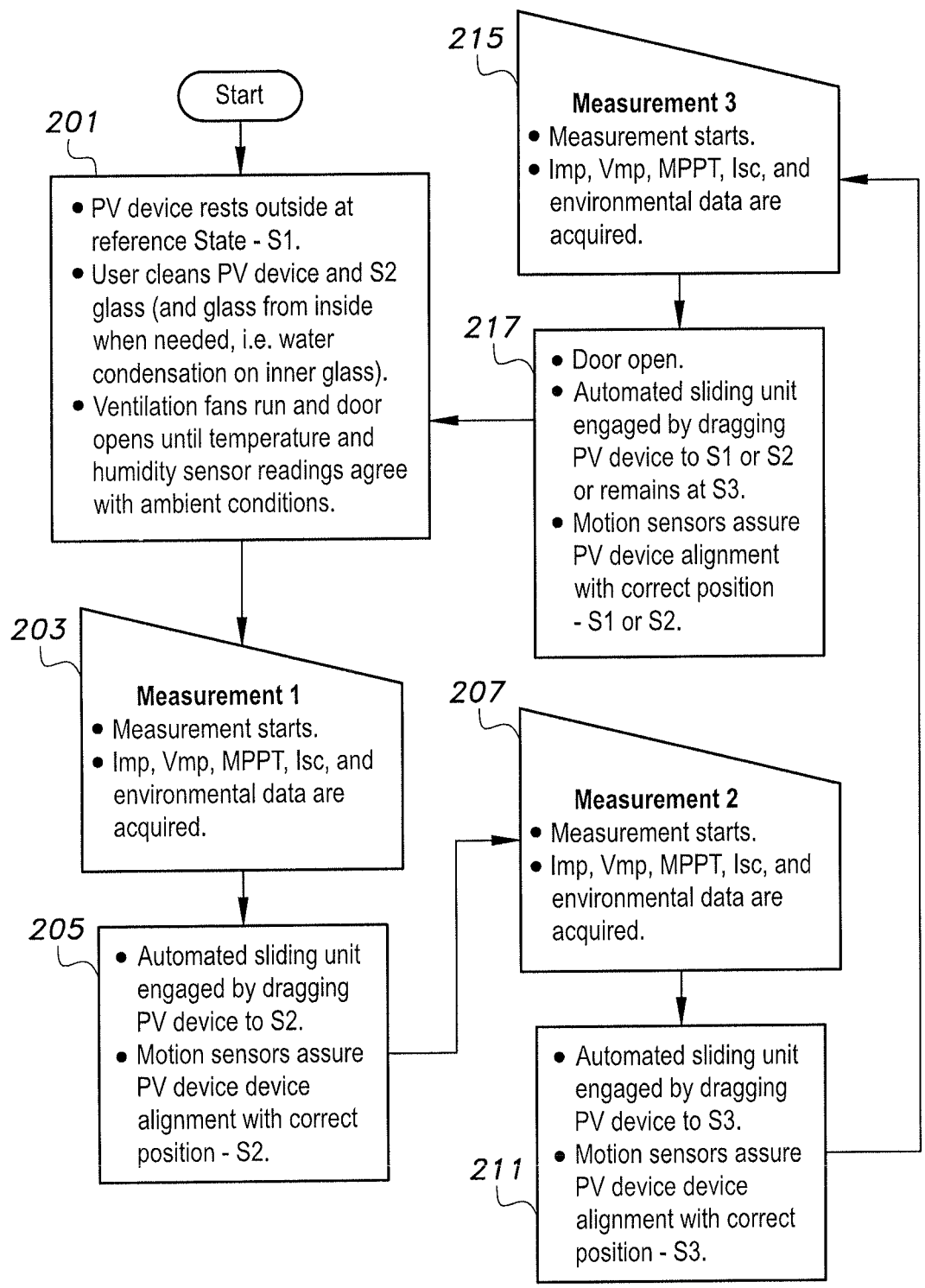
FIG. 2 is a flowchart showing mechanical steps in taking of measurements in three measurement states in a measurement cycle.

FIG. 2 is a flowchart showing one variation of the mechanics of taking measurements in States 1, 2 and 3. In each test sequence, testing is performed for short circuit current ($I_{sc}$), maximum power ($P_{max}$), and/or other criteria of the DUT component 113. Environmental data is also taken.

Referring to FIG. 2, the DUT is initially placed in a position outside the enclosure 127 of the device 101, and the test station 122 is cleaned, if needed (step 201). Measurement 1 is then taken (step 203). The DUT is then moved (step 205) into the enclosure 127 of the device 101 at test station 122 for testing in a clean state, as Measurement 2. The difference is that substantially all factors imposed by enclosing the DUT in enclosure 127 are present. The DUT is then tested (step 207). The DUT is then moved (step 211) for testing (step 215) in a soiled state, as Measurement 3. In the soiled state, the device's third test station 123 is either naturally soiled with dust and other environmental debris, or simulated dirt can be used at test station 123, and measurements are taken under those conditions (step 215), which is Measurement 3.

In an automated process, the DUT is placed in a position outside the enclosure of the device 101, and automated movement is achieved by motor controls to move the support tray 135. The support tray 135 transports the DUT for Measurements 1, 2, and 3 (with Measurement 1 performed before movement). This provides an automated acquisition of measurements for each test station where the DUT is evaluated.

On completion of the measurements, after obtaining Measurement 3 (step 215), the DUT is moved (step 217) to rest either at station 1, station 2, or remain at station 3 between measurement cycles.

One difference between Measurements 1 and 2 is that a baseline is established to account for losses due to the construction of the device 101 itself. In that way, the measurements taken under the regimes of Measurements 2 and 3 represent the changes resulting from the soiling represented by Measurement 3, with the effects of the device 101 cancelled out by the difference between Measurements 1 and 2.

Figure 3A:
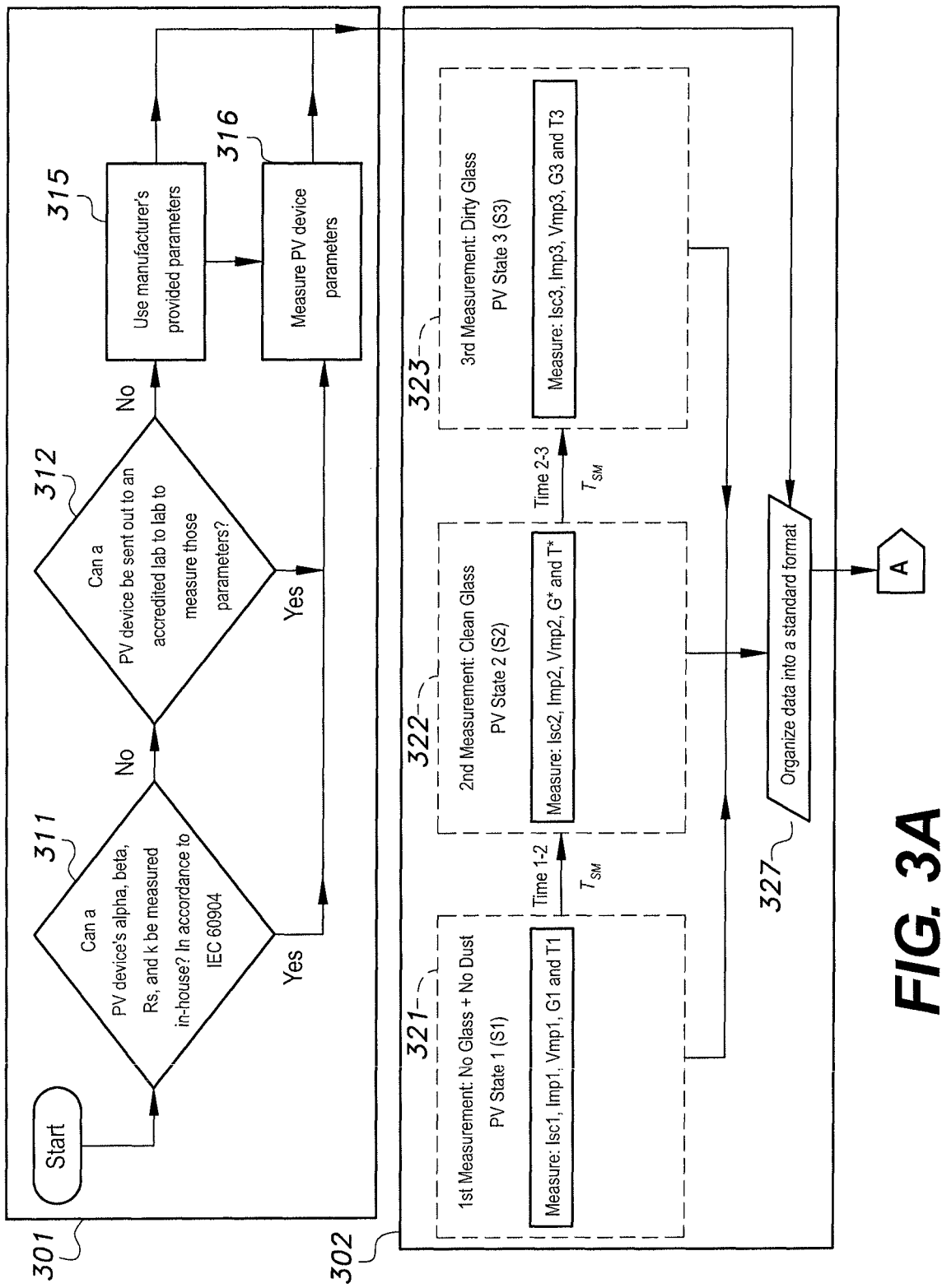
FIG. 3A, FIG. 3B, and FIG. 3C are a flowchart showing the steps in a method for measuring the effect of soiling on a photovoltaic device.
Figure 3B:
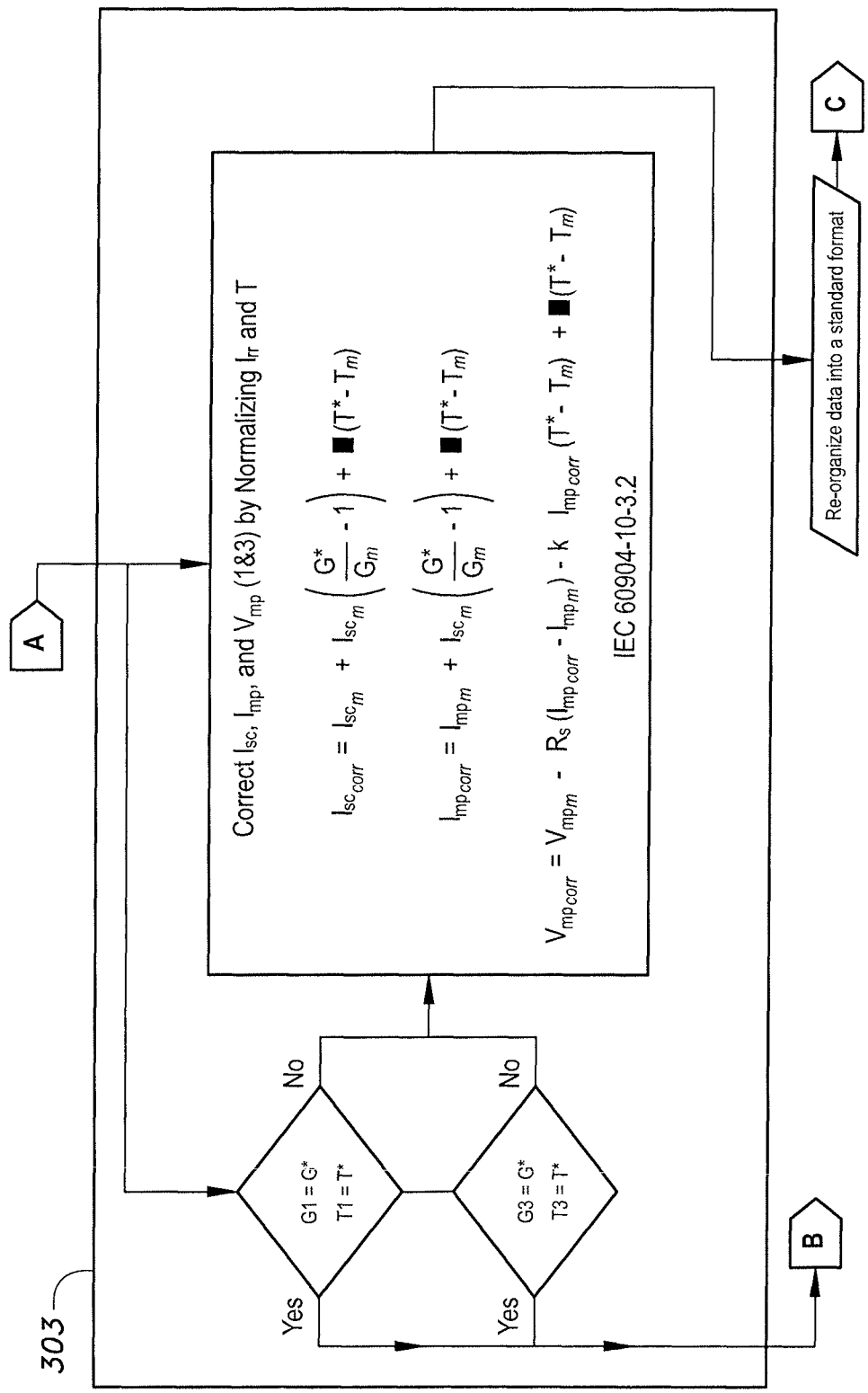
Figure 3C:
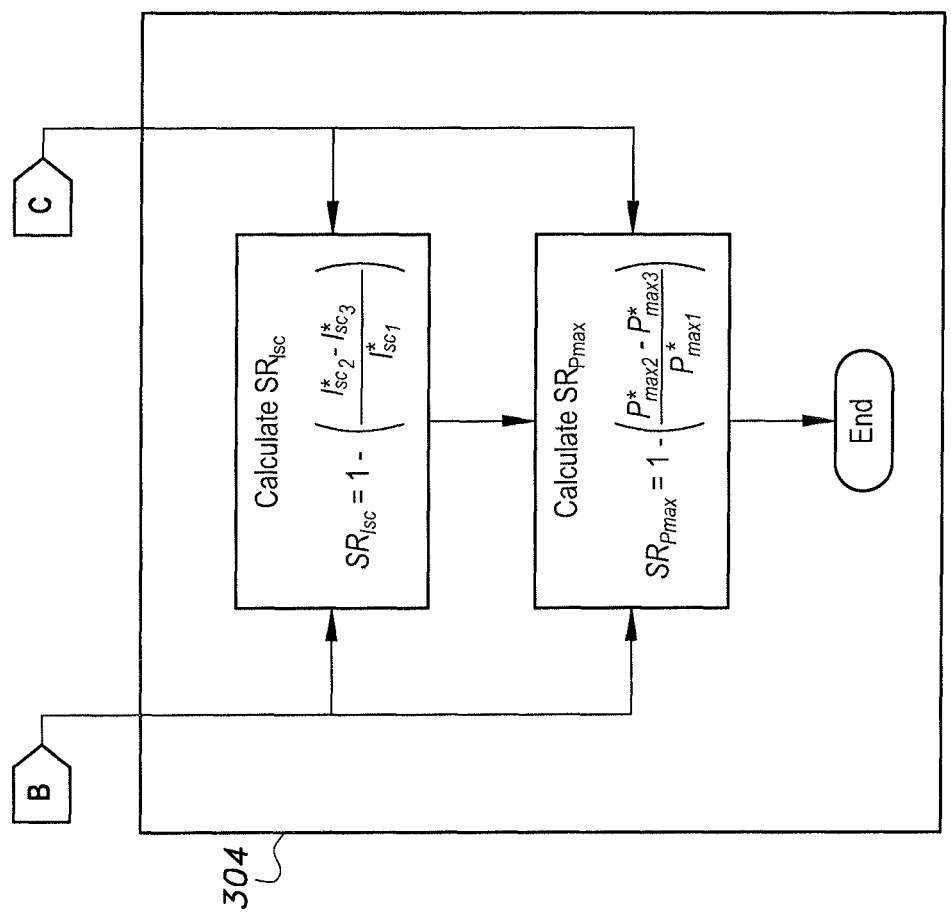

FIGS. 3A-3C are flowcharts showing the procedures and setup required for obtaining soiling measurements when using a single PV device. The process includes pre-installation 301, field measurements and data acquisition 302, normalizing weather conditions to a reference state 303 (i.e., State 2), and computation of the soiling ratio (SR) 304.

In the pre-installation step 301, a determination (step 311) is made of the ability to measure the PV device's alpha, beta, Rs and k values. Ideally, these values can be measured in the lab (in-house measurements) in accordance with IEC 60904. If it is not possible to obtain some of these measurements, a determination (step 312) is made as to whether measurements can be obtained from other accredited labs or supplied from another source. In either case, if these measurements cannot be made, then manufacturer-supplied parameters are used (step 315). If these values can be measured, then the device parameters are measured (step 316). Similarly, if some, but not all, parameters can be measured, then these parameters are used in combination with manufacturer-supplied parameters.

The parameters are provided for use in field measurements and data acquisition 302. Three measurements are used to obtain values for States 1, 2 and 3. In State 1, the measurement is taken with no transparent cover and the DUT is substantially clean (step 321). In State 2, a measurement is taken with clean transparent cover (step 322), and in State 3, a measurement is taken with soiled transparent cover (step 323). The measured data is organized into a standard format (step 327).

After obtaining the data for each of States 1, 2 and 3, normalized for weather conditions (step 303), a computation is made of a soiling ratio. In the normalization according to weather conditions (step 303), adjustments are made so that weather conditions as would affect the measurements are taken for State 2. These same adjustments are then applied to States 1 and 3. The normalized data is re-organized into a standard format (step 367) for use in the process for computing the soiling ratio (SR) (step 304).

Additional functions may be implemented within the scope of this disclosure, which may include combining an automatization capability to periodically clean the "clean transparent cover" (required step) in addition to manual cleaning; providing an ability to both manually and automatically move the PV device from States 1, 2 and 3; development of a universal design to accommodate all PV sizes; combining the device with a weather station; moving the transparent cover of stations 2 and 3 over the fixed DUT at station 1 to make the three sequential measurements required; and combining the device with a solar simulator for indoor testing.

Figure 4:
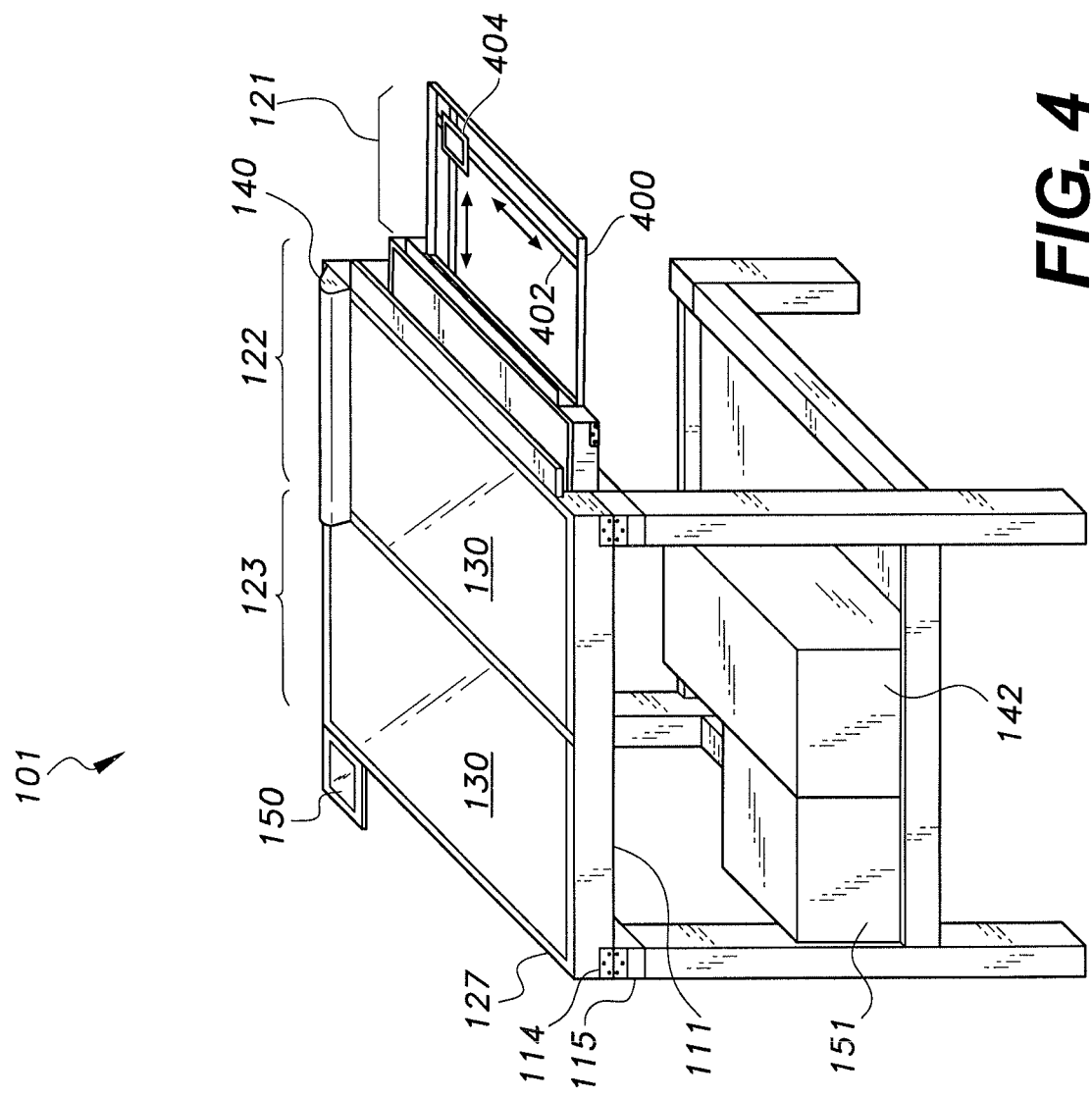
FIG. 4 is a perspective view of an alternative embodiment of the device for measuring the effect of soiling on a photovoltaic device, largely schematic, and for additionally spatially resolving soiling non-uniformity.
Figure 5:
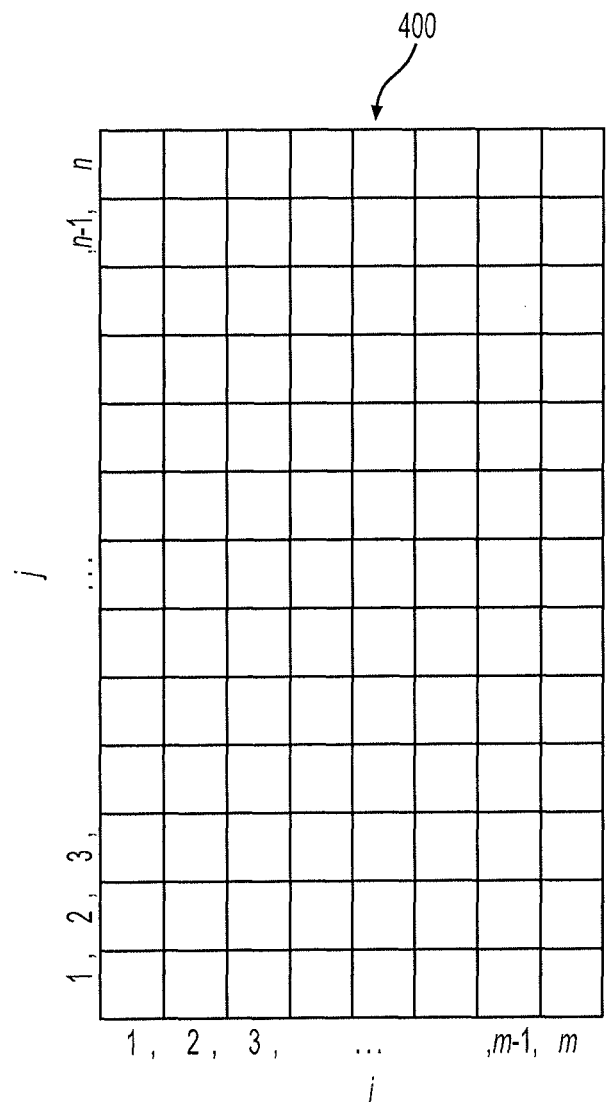
FIG. 5 diagrammatically illustrates division of a transparent cover into cells of a Cartesian grid for an alternative method for spatially resolving soiling non-uniformity on a photovoltaic device.

In the alternative embodiment of FIG. 4, the relatively basic support tray 135 of the previous embodiment is replaced by support tray 400, which includes an x-y stage 402 for moving a PV test device 404 in a two-dimensional plane. It should be understood that any suitable type of x-y stage, or any other suitable mechanism for selective, two-dimensional positioning of the PV test device 404 on the support tray 400 may be utilized. The diagram of FIG. 5 illustrates the support tray 400 (or equivalently, the transparent cover 130 disposed over the third station 123, which measures $P_{max}$ or $I_{SC}$ for a cover 130 that is soiled and never cleaned) divided into an m×n two-dimensional rectangular array. Although only eight columns (arrayed in the i-direction) and thirteen rows (arrayed in the j-direction) are shown in FIG. 5, it should be understood that the grid of FIG. 5 is shown for exemplary and illustrative purposes only, and that m and n may each have any desired value (depending on how small DUT 404 is and/or the area of component 130). The x-y stage 402 is used to move the PV test device 404 to desired Cartesian cell coordinates of the support tray 400 for measurement. Thus, rather than measuring an overall soiling ratio (SR), as in the previous embodiment, individual localized SRs can be measured. Particularly, the value of $I_{sc}$ and/or $P_{max}$ is measured sequentially at all of the different or individual (i,j) coordinates.

Testing is performed in a similar manner to that described above, with the testing at stations 121 and 122 remaining unchanged. The x-y stage 402 is used at station 123 for the State 3 measurements. In the previous embodiment, a single State 3 measurement was made at station 123. Using the x-y stage 402 of FIG. 4, sequential SR measurements are made to produce a two-dimensional SR matrix of the tested soiled area at the third station 123. The $I_{sc}$ and $P_{max}$ measurements at stations 121 and 122 are taken only once, as in the previous embodiment, but a total of N measurements are taken at station 123, where N=m×n, and the x-y stage 402 is used to move the PV test device 404 through the various (i,j) coordinates, where 1≤i≤m and 1≤j≤n. Thus, for the State 3 testing, the measurements taken are $I_{sc1}$-$P_{max1}$, $I_{sc2}$-$P_{max2}$, . . . , $I_{scN}$-$P_{maxN}$.

At each coordinate point (i,j), the measured SR is given by:

$$SR_{Pmax(i,j)} = \frac{P_{max(i,j)} + (P_{max1} - P_{max2})}{P_{max1}}; \text{ and} \quad (1)$$

$$SR_{Isc(i,j)} = \frac{I_{sc(i,j)} + (I_{sc1} - I_{sc2})}{I_{sc1}}. \quad (2)$$

As shown in FIG. 4, the PV test device 404 used for testing the uniformity of PV soiling at a particular location may have dimensions or a relative surface area substantially equal in area to a single grid square of the m×n Cartesian grid shown in FIG. 5. At this stage, the effort is to obtain a 2-dimensional Soiling Ratio matrix of the area of the transparent cover 130 that is exposed to soiling at the third testing station 123 of the device 101. The PV test device 404 may be moved sequentially from one grid location to the next as maximum power and short circuit current measurements are made by stepper motors or the like in any desired pattern. For example, measurements may be made across the bottom row, keeping j=1 while cycling through columns i=1 to m, then incrementing the row to j=2 and cycling through columns i=1 to m, etc., ending with the top row where j=n. Controllers and stepper motors for scanning through a grid in this manner are well known for various applications, e.g., plotters and the like.

Figure 6:
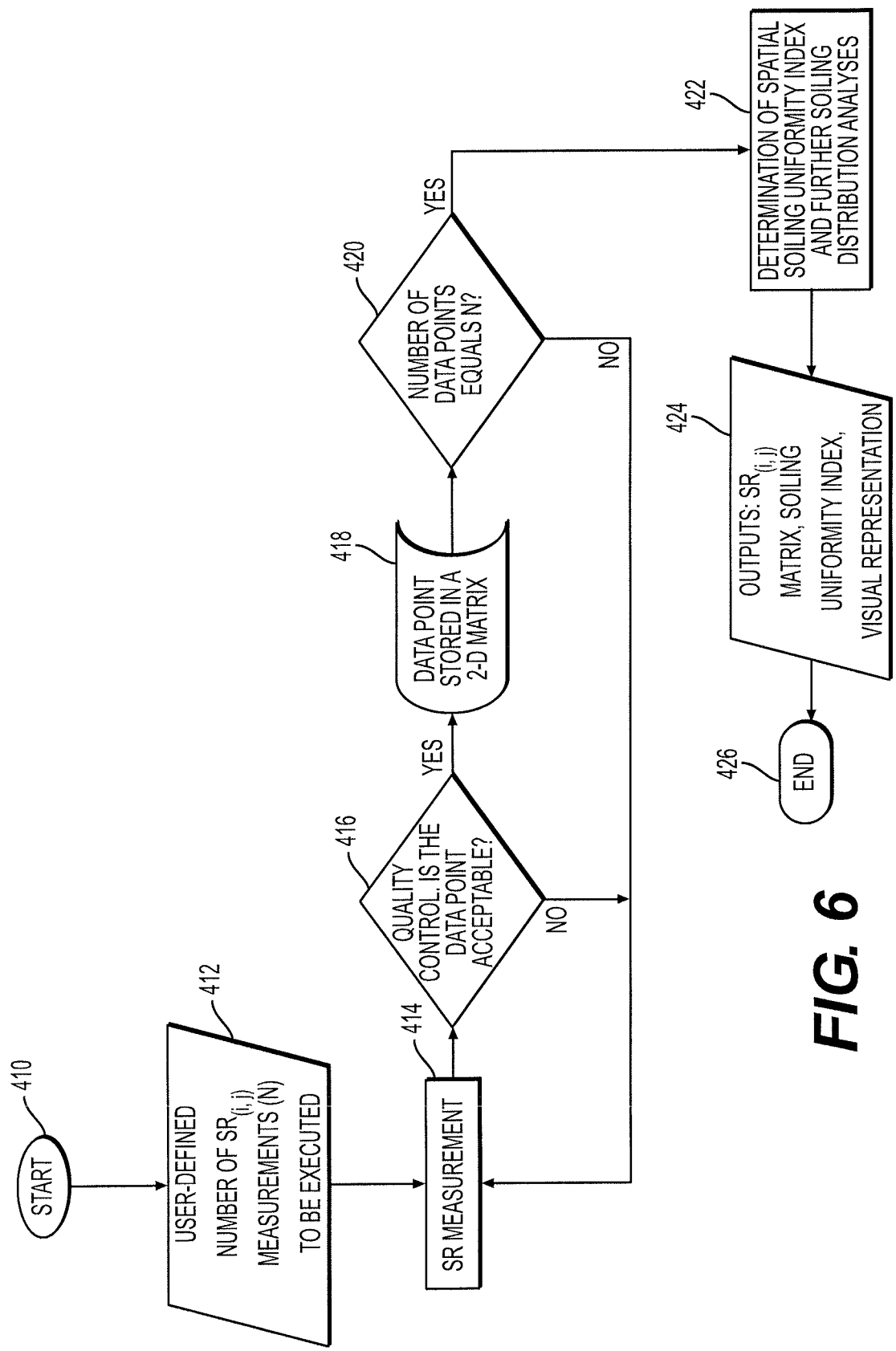
FIG. 6 is a flowchart showing steps of the alternative method for spatially resolving soiling non-uniformity on a photovoltaic device.

The process control is shown in FIG. 6, with the process beginning at 410. At step 412, the user inputs the desired number N of $SR_{(i,j)}$ measurements to be taken. The SR measurements are taken at step 414, and quality control is performed at step 416 to determine if the measured and recorded data point is within acceptable tolerances. If not, another measurement is taken. If the data point is acceptable, then the data is stored in the two-dimensional matrix being constructed (step 418) and a determination is made if all N data points have been recorded yet (step 420). If N data points have not been added to the matrix, then another measurement (going back to step 414) is taken. If all N data points have been recorded, then a spatial soiling uniformity index is determined, as well as performance of any additional soiling distribution analyses (step 422). The $SR_{(i,j)}$ matrix, the soiling uniformity index and a visual representation of soiling are output to the user at step 424, and the process ends at 426.

With regard to the calculation of the soiling uniformity index (SUI), the SUI is an indicator of spatial soiling uniformity of a PV area under test (i.e., a single PV module's surface or a PV plant site), with values ranging from 0 to 1 inclusive, such that the minimum value (i.e., a value of zero) represents highly non-uniform soiling, and a maximum value (i.e., a value of one) represents ideal uniform soiling. In a first statistical approach for calculating the SUI, conventional uniformity calculations, such as those applied in a wide variety of different fields, are used. This first statistical approach is mainly applicable when a large population of SR values is available.

Assuming that a single iteration of SR measurements, as described above, have been taken to populate the SR matrix, the SR values are arranged in an ascending order and then divided into four quartiles. The average of the lowest quartile is then divided by the average total SR value. This provides an indication of how the most severe SR quartile would deviate from the mean SR value, thus providing a generic indication on soiling non-uniformity in the sample. Thus, SUI may be calculated as:

$$SUI = \frac{\overline{SR}_{LQ}}{\overline{SR}_t}, \quad (3)$$

where 0≤SUI≤1, $\overline{SR}_{LQ}$ is the average SR value of the lowest quartile, and $\overline{SR}_t$ is the mean SR of the total sample.

Figure 7:
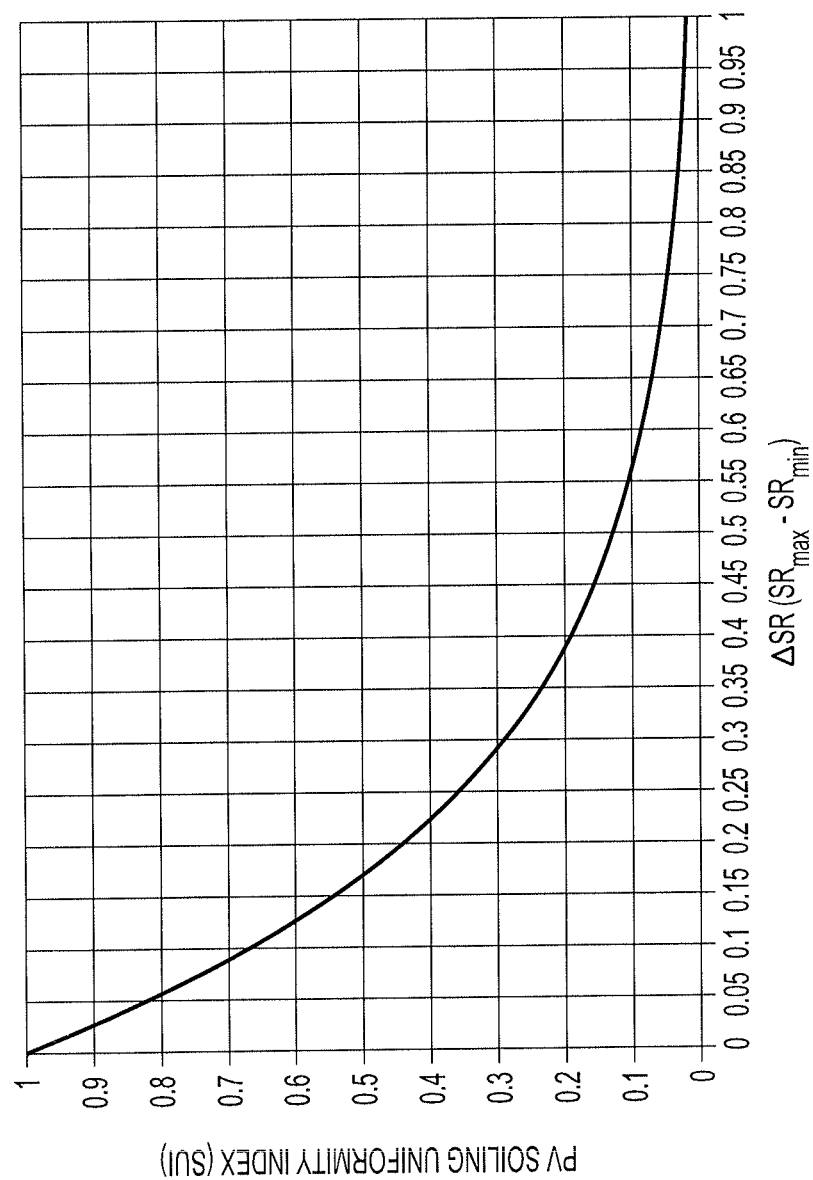
FIG. 7 is an exemplary plot of soiling uniformity index as a function of the differential between maximum soiling ration and minimum soiling ratio in the alternative method for spatially resolving soiling non-uniformity over a photovoltaic area under test (i.e., a single PV module's surface or a PV plant site).

In a second statistical approach, the two extreme SR values (i.e., the lowest and highest SR values) are considered, regardless of the population size and spread of the SR values. This approach has practical applicability to situations where the extreme SR values are not considered as sample outliers but, rather, as determinant factors. Such a case, for example, is found in PV power plants where a single module's high soiling non-uniformity would affect the production of every other module connected to it in series. Thus, the highest and lowest soiling ratio values, $SR_{max}$ and $SR_{min}$, respectively, can be fitted exponentially with actual power plant operation thresholds accounted for. FIG. 7 shows such an exponential decay, which serves as a universal PV soiling uniformity index that could conveniently inform practitioners of the non-uniform soiling severity.

In the base-intercept form (i.e., the basic form of exponential functions), a physical indication relevant to this application can be deduced as:

$$y = P_0 \alpha^x, \quad (4)$$

where $P_0$ is the y-intercept, which resembles the extreme theoretical conditions at which the uniformity is ideal (i.e., when it equals one), and α is the base (i.e., analogous to the slope of the line), which determines how the curve moves towards the x-axis.

In terms of the SUI, α introduces the operational thresholds into the index. Two thresholds may be chosen based on plant operators' conventions. The first is at 5% power loss between two PV devices due to non-uniformity, i.e., $\Delta SR = SR_{max} - SR_{min} = 0.05$, which correlates to an SUI of 0.8. The second threshold, defined as the extreme effect of non-uniformity, is set at $\Delta SR = 0.01$ (i.e., 10% power loss), which correlates to an SUI of 0.65. Using these two points on the exponential function, the base a is found as follows:

$$y_1 = P_0 \alpha^{x_1}, \quad (5)$$

$$y_2 = P_0 \alpha^{x_2},$$

$$\therefore \alpha = \left(\frac{y_2}{y_1}\right)^{\frac{1}{x_2-x_1}},$$

where x represents the ΔSR intervals that define the SUI's behavior as the SR difference increases. Using the above exemplary case, the intervals were set at 0.05 deviations from the ideal $SR_{max}$=1. Based on the above exemplary plant parameters, $$\alpha = \left(\frac{0.65}{0.80}\right)^{20} = 0.01572.$$

Figure 8:
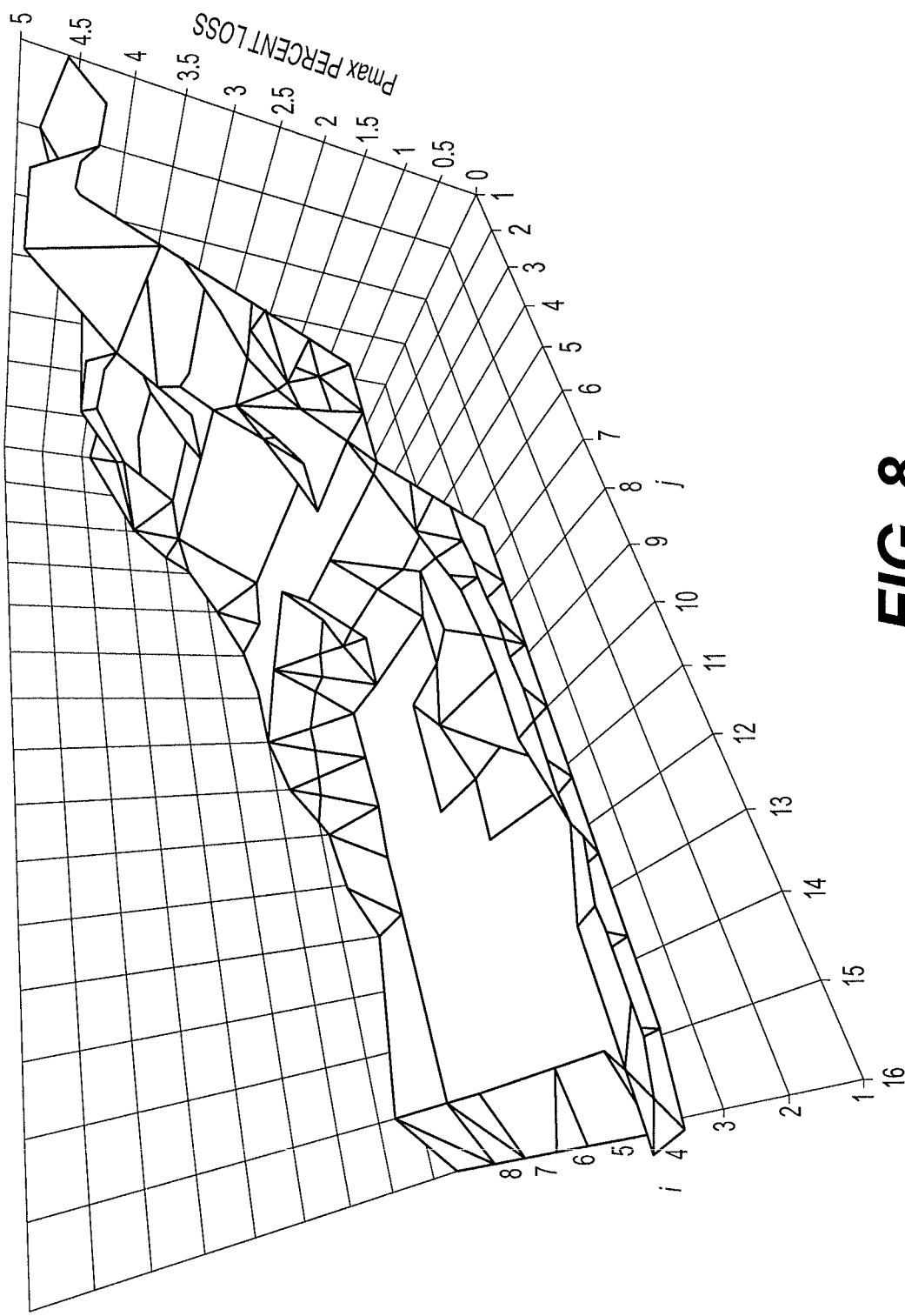
FIG. 8 is an exemplary three-dimensional surface plot showing spatial soiling distribution produced by the alternative method for spatially resolving soiling non-uniformity on a photovoltaic device.

From the above, equation (4) results in the following PV soiling uniformity index:

$$SUI = \alpha^{(SR_{max} - SR_{min})}, \quad (6)$$

where, as defined above, the values of SUI range from 0 to 1 inclusive, such that the minimum value (i.e., a value of zero) represents highly non-uniform soiling, and a maximum value (i.e., a value of one) represents uniform soiling. FIG. 8 represents a three-dimensional surface plot of spatial soiling distribution on a PV surface, where the vertical axis in FIG. 8 represents $SR_{(i,j)}$ in terms of $P_{max}$ losses, and the horizontal axes represent the (i,j) coordinates.

It is to be understood that the device and method for measuring the effect of soiling on a PV device are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for spatially resolving soiling non-uniformity on a photovoltaic device, comprising the steps of:
   making measurements of at least one electrical parameter of a single photovoltaic device corresponding to the photovoltaic device's effectiveness in generating electricity in response to exposure to illumination in three different states, the measurements being made sequentially in a single measurement cycle, the first state being with the photovoltaic device unobstructed and exposed directly to illumination, the second state being with the photovoltaic device disposed in a compartment exposed to illumination through a transparent cover cleaned regularly, and the third state being with the photovoltaic device disposed in a compartment exposed to illumination through a transparent cover on which natural or simulated soil is permitted to accumulate without cleaning;
   in the third state, systematically stepping the single photovoltaic device through cells of an m×n Cartesian coordinate grid corresponding to the transparent cover on which natural or simulated soil is permitted to accumulate without cleaning while making the measurements of the at least one electrical parameter in each of the cells, wherein m and n are each integers greater than or equal to one;
   calculating a soiling ratio (SR) from the at least one electrical parameter measured in each of the cells to define a 2-dimensional matrix of soiling ratios corresponding to Cartesian locations (i,j) in the compartment in which the single photovoltaic device is exposed to illumination through the transparent cover on which natural or simulated soil is permitted to accumulate without cleaning, wherein i and j are each integers such that 1≤i≤m and 1≤j≤n; and
   comparing the calculated soiling ratios in the 2-dimensional matrix to identify areas of the transparent cover on which natural or simulated soil is permitted to accumulate without cleaning where non-uniform distribution of soiling increases risks of electrical mismatch between interconnected solar cells, hotspots, and other photovoltaic device faults.

2. The method for spatially resolving soiling non-uniformity on a photovoltaic device as recited in claim 1, wherein the transparent covers in the second and third states are made of tempered photovoltaic (PV) glass.

3. The method for spatially resolving soiling non-uniformity on a photovoltaic device as recited in claim 1, wherein the at least one electrical parameter is maximum power, the step of calculating a soiling ratio (SR) further comprising the step of calculating:

$$SR_{Pmax(i,j)} = \frac{P_{max(i,j)} + (P_{max1} - P_{max2})}{P_{max1}}$$

where $S_{RPmax(i,j)}$ is a Soiling Ratio for the Cartesian cell (i,j) calculated from measurements of maximum power, $P_{max(i,j)}$ is the maximum power measured for the Cartesian cell (i,j), and $P_{max1}$ and $P_{max2}$ are measurements of maximum power in the first state and the second state, respectively.

4. The method for spatially resolving soiling non-uniformity on a photovoltaic device as recited in claim 3, further comprising the step of calculating a soiling loss indicator (SL) for each of the Cartesian cells, wherein SL=(1−$SR_{Pmax(i,j)}$).

5. The method for spatially resolving soiling non-uniformity on a photovoltaic device as recited in claim 1, wherein the at least one electrical parameter is short circuit current, the step of calculating a soiling ratio (SR) further comprising the step of calculating:

$$SR_{Isc(i,j)} = \frac{I_{sc(i,j)} + (I_{sc1} - I_{sc2})}{I_{sc1}}$$

where $SR_{Isc(i,j)}$ is a Soiling Ratio calculated from measurements of short circuit current, $I_{sc(i,j)}$ is the short circuit current measured for the Cartesian cell (i,j), and $I_{sc1}$ and $I_{sc2}$ are measurements of short circuit current made in the first state and the second state, respectively.

6. The method for spatially resolving soiling non-uniformity on a photovoltaic device as recited in claim 5, further comprising the step of calculating a soiling loss indicator (SL) for each of the Cartesian cells, wherein SL=(1−$SR_{Isc(i,j)}$).

7. The method for spatially resolving soiling non-uniformity on a photovoltaic device as recited in claim 1, further comprising the step of, for each of the measurements, plotting a current-voltage (IV) curve of the single photovoltaic device.

8. The method for spatially resolving soiling non-uniformity on a photovoltaic device as recited in claim 1, further comprising the step of calculating a soiling uniformity index based on the soiling ratios.

9. The method for spatially resolving soiling non-uniformity on a photovoltaic device as recited in claim 8, wherein the step of calculating the soiling uniformity index comprises the steps of:
   arranging the soiling ratios in ascending order;
   dividing the arranged soiling ratios into quartiles;
   calculating an average soiling ratio of the lowest one of the quartiles, $\overline{SR}_{LQ}$;
   calculating a total average soiling ratio of a cumulative total of all of the soiling ratios, $\overline{SR}_t$; and
   calculating the soiling uniformity index, SUI, as:

$$SUI = \frac{\overline{SR}_{LQ}}{\overline{SR}_t}$$

wherein 0≤SUI≤1.

10. The method for spatially resolving soiling non-uniformity on a photovoltaic device as recited in claim 8, wherein the step of calculating the soiling uniformity index comprises the steps of:
   determining a maximum soiling ratio, $SR_{max}$, from the calculated soiling ratios;
   determining a minimum soiling ratio, $SR_{min}$, from the calculated soiling ratios; and
   calculating the soiling uniformity index, SUI, as:

$$SUI = \alpha^{(SR_{max} - SR_{min})}$$

wherein α is an exponential curve-fitting base.

11. The method for spatially resolving soiling non-uniformity on a photovoltaic device as recited in claim 10, wherein α=0.01572.

12. A device for spatially resolving soiling non-uniformity on a photovoltaic device, comprising a housing defining:
   a first partially enclosed compartment adapted for supporting the photovoltaic device under test, the first partially enclosed compartment being exposed directly to illumination of the photovoltaic device under test without any cover or obstruction;
   a second enclosed compartment adapted for supporting the photovoltaic device under test, the second enclosed compartment having a transparent cover providing for illumination of the photovoltaic device under test, the transparent cover of the second compartment being adapted for a wide range of cleaning frequency; and
   a third enclosed compartment adapted for supporting the photovoltaic device under test, the third enclosed compartment having a transparent cover providing for illumination of the photovoltaic device under test, the transparent cover of the third compartment being adapted for permitting natural or simulated soil to accumulate on the transparent cover;
   a test circuit configured for measuring an electrical parameter of the photovoltaic device corresponding to the photovoltaic device's effectiveness in generating electricity in response to exposure to illumination;
   an x-y tray configured for selectively positioning the photovoltaic device under test at selected Cartesian cell coordinates within the third enclosed compartment;
   a control circuit connected to the test circuit for controlling the test circuit to make measurements of the electrical parameter sequentially while the photovoltaic device under test is in the first compartment, the second compartment, and the third compartment, respectively, the measurements in the third compartment including measurements of the electrical parameter in each of the Cartesian cells; and
   a tilt mechanism capable of adjusting a tilt angle of the first partially enclosure compartment, the second enclosed compartment, the third enclosed compartment, and the photovoltaic device concurrently between 0° to 90°, either manually or automatically.

13. The device for spatially resolving soiling non-uniformity on a photovoltaic device as recited in claim 12, wherein the transparent cover of said second compartment and the transparent cover of said third compartment each comprise tempered photovoltaic (PV) glass.

14. The device for spatially resolving soiling non-uniformity on a photovoltaic device as recited in claim 12, wherein said test circuit and said control circuit are further configured for measuring and test circuit testing for current at maximum power (Imp), voltage at maximum power (Vmp), Maximum Power Point (MPP) and, short circuit output current (Isc), and for plotting a current-voltage (IV) curve of the single photovoltaic device for each of the three measurements.

15. The device for spatially resolving soiling non-uniformity on a photovoltaic device as recited in claim 12, further comprising:
   at least one temperature sensor selected from the group consisting of a thermocouple and a resistance temperature detector, the at least one temperature sensor being connected to said controller circuit; and
   at least one irradiance sensor selected from the group consisting of a pyranometer and a reference PV device, the at least one irradiance sensor being connected to said controller circuit;
   wherein said controller circuit is configured for controlling said test circuit to make the three measurements in quick succession to minimize PV temperature and irradiance deviations between the measurements.

16. The device for spatially resolving soiling non-uniformity on a photovoltaic device as recited in claim 15, wherein said controller circuit is configured for normalizing the measured data for temperature, weather and other ambient conditions.

17. The device for spatially resolving soiling non-uniformity on a photovoltaic device as recited in claim 12, further comprising a washing unit mounted on said housing and connected to said controller circuit, the controller circuit being configured to activate the washing unit to:
   wash the photovoltaic device when in the first partially enclosed compartment and to wash the transparent cover of the second enclosed compartment with sufficient frequency to ensure accurate measurement; and
   wash the transparent cover of the third enclosed compartment to reset the soiling monitoring cycle.

18. The device for spatially resolving soiling non-uniformity on a photovoltaic device as recited in claim 12, wherein the electrical parameter is maximum power, the test circuit being configured for measuring maximum power, the control circuit being further configured for calculating:

$$SR_{Pmax(i,j)} = \frac{P_{max(i,j)} + (P_{max1} - P_{max2})}{P_{max1}}$$

where $SR_{Pmax(i,j)}$ is a Soiling Ratio for the Cartesian cell (i,j) calculated from measurements of maximum power, $P_{max(i,j)}$ is the maximum power measured for the Cartesian cell (i,j), and $P_{max1}$ and $P_{max2}$ are measurements of maximum power in the first state and the second state, respectively.

19. The device for spatially resolving soiling non-uniformity on a photovoltaic device as recited in claim 12, wherein the electrical parameter is short circuit current, the test circuit being configured for measuring short circuit current, the control circuit being further configured for calculating:

$$SR_{Isc(i,j)} = \frac{I_{sc(i,j)} + (I_{sc1} - I_{sc2})}{I_{sc1}}$$

where $SR_{Isc(i,j)}$ is a Soiling Ratio calculated from measurements of short circuit current, $I_{sc(i,j)}$ is the short circuit current measured for the Cartesian cell (i,j), and $I_{sc1}$ and $I_{sc2}$ are measurements of short circuit current made in the first state and the second state, respectively.

* * * * *